United States Patent
Dinse et al.

(10) Patent No.: US 10,028,714 B2
(45) Date of Patent: Jul. 24, 2018

(54) CONTROL DEVICE, MEDICAL APPARATUS AND METHOD TO CONTROL MOVEMENTS OF THE MEDICAL APPARATUS

(71) Applicant: Siemens Aktiengesellschaft, Munich (DE)

(72) Inventors: Franziska Dinse, Heiligenstadt (DE); Bjoern Michelsen, Kitzingen (DE); Juliane Ritter, Neunkirchen (DE)

(73) Assignee: Siemens Aktiengesellschaft, Munich (DE)

( * ) Notice: Subject to any disclaimer, the term of this patent is extended or adjusted under 35 U.S.C. 154(b) by 974 days.

(21) Appl. No.: 14/495,098

(22) Filed: Sep. 24, 2014

(65) Prior Publication Data
US 2015/0085986 A1  Mar. 26, 2015

(30) Foreign Application Priority Data
Sep. 24, 2013 (DE) .................. 10 2013 219 155

(51) Int. Cl.
*A61B 6/00* (2006.01)
*A61B 6/10* (2006.01)

(52) U.S. Cl.
CPC ............... *A61B 6/467* (2013.01); *A61B 6/10* (2013.01); *A61B 6/54* (2013.01); *A61B 6/548* (2013.01); *A61B 6/4441* (2013.01)

(58) Field of Classification Search
CPC ..................................................... A61N 5/10
See application file for complete search history.

(56) References Cited

U.S. PATENT DOCUMENTS

| | | | | |
|---|---|---|---|---|
| 6,348,911 B1 * | 2/2002 | Rosenberg | ............. | A63F 13/06 318/568.11 |
| 6,630,799 B2 * | 10/2003 | Fleming | ................. | A61L 2/082 315/205 |
| 6,765,987 B2 * | 7/2004 | Fleming | ............... | A61L 2/0041 378/105 |
| 6,785,358 B2 * | 8/2004 | Johnson | ............... | A61B 5/7475 378/115 |
| 7,016,469 B2 * | 3/2006 | Johnson | ............... | A61B 5/7475 378/115 |
| 7,634,308 B2 * | 12/2009 | Ogawa | ................... | A61B 6/481 378/196 |
| 8,641,663 B2 * | 2/2014 | Kirschenman | ..... | A61B 17/2909 604/156 |
| 9,492,131 B2 * | 11/2016 | Meek | .................... | A61B 6/4482 |
| 9,642,584 B2 * | 5/2017 | Niebler | ................ | A61B 6/4441 |
| 2002/0131554 A1 * | 9/2002 | Fleming | ................ | A61L 2/0041 378/119 |

(Continued)

FOREIGN PATENT DOCUMENTS

DE    102009058509 A1    6/2011

*Primary Examiner* — Thomas R Artman
(74) *Attorney, Agent, or Firm* — Schiff Hardin LLP

(57) ABSTRACT

In a method to control movements of a medical apparatus via a control device with a touch-sensitive display, an apparatus component of the medical apparatus is selected and; and move the selected apparatus component is moved according to commands made at the touch-sensitive display. A safety loop must be closed in order to activate the movement of the apparatus component. A control device to control a medical apparatus, and a medical apparatus having at least one apparatus component, operate according to this method.

7 Claims, 3 Drawing Sheets

(56) References Cited

U.S. PATENT DOCUMENTS

| | | | | |
|---|---|---|---|---|
| 2002/0131555 | A1* | 9/2002 | Fleming | A61L 2/082 378/119 |
| 2003/0068011 | A1* | 4/2003 | Johnson | A61B 5/7475 378/115 |
| 2004/0127789 | A1* | 7/2004 | Ogawa | A61B 6/481 600/425 |
| 2005/0004802 | A1* | 1/2005 | Johnson | A61B 5/7475 704/275 |
| 2013/0088452 | A1 | 4/2013 | Glaser-Seidnitzer et al. | |
| 2013/0230142 | A1* | 9/2013 | Murata | A61B 6/4405 378/62 |
| 2015/0085986 | A1* | 3/2015 | Dinse | A61B 6/10 378/98 |
| 2015/0216489 | A1* | 8/2015 | Everaerts | A61B 6/12 600/424 |

* cited by examiner

CONTROL DEVICE, MEDICAL APPARATUS AND METHOD TO CONTROL MOVEMENTS OF THE MEDICAL APPARATUS

BACKGROUND OF THE INVENTION

Field of the Invention

The invention concerns a method to control movements of a medical apparatus via a control device with a touch-sensitive display, which includes selecting an apparatus component of the medical apparatus and moving the selected apparatus component as well as a control device to control a medical apparatus and a medical apparatus that operate according to such method.

Description of the Prior Art

In various types of medical apparatuses, such as x-ray systems or fluoroscopy systems, at least one apparatus component is most often movable in a motorized manner around at least one axis. Manual control of the movable components plays a large role. For example, it is necessary to position the individual components of an x-ray system (such as x-ray detector and x-ray radiator) relative to a patient so that an x-ray exposure of a defined body part of the patient can be created with an optimally good quality.

Various control methods for the manual control to move the apparatus components are known, BUT the existing solutions have problems that have previously not been solved or have not been considered.

For example, one problem is to apply an existing control method to various apparatuses so that the operation becomes easier for the user upon changing apparatuses, or when applied to a previously unknown apparatus.

An additional unsolved problem is that of allowing blind operability, namely that the user can operate the medical apparatus without looking at the controls at the control device, or without visual contact with the apparatus with the user receiving, at the apparatus itself or at the control device, a direct visual feedback as to whether the movements have been executed.

In addition, existing control methods can be difficult to adapt if, for example, new ideas and changes should be incorporated into the existing concept. Even the incorporation of small changes at the apparatus to be controlled can be very cost-intensive.

The following control methods for the manual control of apparatus components are known in the prior art:

One possibility is control via analog joysticks. Such joysticks are often integrated into a stationary operating console for remote control. If a user moves the joystick in a defined direction, the apparatus component which is assigned to the joystick also moves in the corresponding direction. The joysticks are conventionally movable along one or two axes. The strength of the deflection can affect the movement, in particular how fast a movement is executed. The greater the deflection of the joystick, the faster that the component then moves. One or two hands are necessary to operate the joystick, depending on the complexity of the control.

An additional control method is the use of a remote control with buttons. Analogous to the control by means of joystick, here the various components and axes of the apparatus system are mapped and addressed via buttons. In contrast to the operation with joystick, in which the operation is realized via a stationary operating console (or an operating console with only limited mobility), the remote control is portable, wireless and operable with one hand.

A laser remote control is an additional known control method, in which the system movement is likewise controlled with the use of a wireless remote control. A significant difference relative to the remote control with buttons is that the movements are primarily controlled via movements of the remote control itself, and not by the pressing of buttons.

Furthermore, a controller of medical apparatuses that is based on a touchscreen display is known, for example for a C-arm system. Here the movement, in particular an exact positioning of the C-arm, can be controlled by finger movements on a touch-sensitive display directly attached to the C-arm. The finger movement on the display corresponds to the movement of the C-arm. For example, the velocity of the movement can be affected by the length of the movement executed on the display, or a parallel displacement of the C-arm can be achieved by multiple contact points of the display (for example, contacted simultaneously with multiple fingers).

Furthermore, it is fundamentally relevant to security to always execute the movements of the individual components only with safety monitoring, since unintended and unmonitored movements of the components (many of which are very large and heavy) of the medical apparatuses represent a risk of injury for the operating personnel and the patient.

SUMMARY OF THE INVENTION

An object of the invention is to provide a simple and flexible control method for medical apparatuses, with which the risk of injury due to unmonitored or unintended movements of the apparatus can be eliminated.

A simple and flexible method to control a medical apparatus and its individual components in accordance with the invention includes controlling the movements by a control device with touch display, and providing the control device with an additional safety loop so that intended and monitored movements can be executed only if the safety loop is closed.

The movements of the components are controlled by a touch-sensitive control panel. The touch display—shortened to display in the following—can be operated with either one finger or multiple fingers. Operation with multiple fingers simultaneously has advantages since, for example, parallel component movements can be executed more simply. The input at the display takes place by placement or movement of one or more fingers of the user, and/or by placement or movement of an input element. Such an input element—like a finger—triggers a touch event that is detectable to the touch-sensitive touch display. The display is part of a mobile or stationary control device.

The movements of the apparatus components can in principle be controlled in different ways at the display. One possibility is merely to provide a defined region on the display for the movement control. If the user touches the display with a finger or the input element in this region, a virtual joystick (indicated on the display) appears at the contact point. The joystick is indicated on the display as long as the user maintains the contact. If the user then moves the contact point on the display, a movement of an apparatus component along an axis of the system is triggered with this. The user receives a visual feedback via the virtual joystick in that a portion of the virtual joystick follows the movement of the contact point. The velocity of the movement can be varied in that the contact point on the display is shifted away from its original position. The greater the distance between the initial contact point and the moved contact point, the higher the velocity of the movement. Analogously, the smaller the distance between the initial contact point and the moved contact point, the lower the velocity of the movement. In addition to the velocity, the movement direction can also be controlled at the display. The axis of the apparatus component which is addressed by the virtual joystick varies via variation of the angle of the connecting line between the present contact point and the initial contact point. For example, a movement of the addressed apparatus component can thus also be reversed.

The apparatus component moves as long as the user touches the display. If the user breaks the contact with the display—i.e. if he or she thus removes the finger from the display—the movement of the controlled apparatus is immediately interrupted.

In another embodiment instead of the defined region on the display, the virtual joystick is displayed permanently, either at a predefined position or a position on the display that is to be variably defined by the user. The control of the movements takes place as described in the preceding. In particular, an immediate stop of the apparatus movement also takes place here if the contact with the display is interrupted at any point in time.

For the controller, it is preferable for the user to adopt a hand position encompassed around the control device particularly for mobile control devices. The hand, in particular the finger, of the user touches the display on both sides. For example, the thumb lies on the display on the front side of the control device and the remaining four fingers are located on the back side of the control device.

A part of the hand which is not required for control, for example the four fingers on the back side of the control device, is used to close the additional safety loop. This principle for closing the safety loop is also designated as a dead man's switch or dead man's device or dead man's grip. With a one-handed operation of the control device, for example, the other hand of the user that is not used for control can close the safety loop.

The safety loop or the closure thereof can be executed differently. For example, a switch mounted on the back side or lateral side in the form of a capacitive sensor or a button can be used for closing the safety loop. The sensors can also be attached on the front side of the control device, for example as defined regions of the touch-sensitive display.

In order to ensure the safety of the user and the patient in the control of the medical apparatus, the movement of the apparatus components by the control device is possible only when the safety loop is closed, i.e. if a finger of the user touches the capacitive sensor, for example. As soon as the safety loop is no longer closed (thus the user lets go of the control device, for example) the movements of the apparatus are immediately interrupted. An unmonitored and unintended movement of apparatus components is prevented in this way.

A control device with a touch-sensitive display and an additional safety loop, as described above, is suitable both for mobile and stationary applications. In a mobile application, the control device can be used in the form of a wireless remote control that the user holds in his or her hand, or can be attached to a movable control station which is likewise mobile in a certain radius. Both types afford the user a greater freedom of movement in the control of the medical apparatus. For example, upon aligning an x-ray system the user can check its position from all sides by walking around the apparatus and simultaneously executing additional position changes or movements with the mobile control device. Furthermore, the mobile application allows both a one-handed operation and a two-handed operation of the control device. A two-handed operation allows the user to control parallel movements, for example. With a two-handed operation, the control device can be gripped so that the thumbs lie on the display and thus are used to control (meaning to execute) the movements on the display.

In contrast, for stationary operation of the control device the movement radius of the user is severely limited. Here the control device can be attached either directly to the medical apparatus to be controlled or to a stationary control panel.

A combination of mobile and stationary operation is possible, for example by mounting the control device in a docking station. When the control device is located in the docking station, it can be charged and thereby be used as a stationary device. The control device should thereby be positioned in the docking station so that both one-handed and two-handed operation is possible, as for the mobile usage. For example, the control device can simply be placed on the docking station, or it is attached by means of a ball joint with telescoping rod or via clamping. It is important that a switch mounted on the back side to close the safety loop is not covered by the docking station and furthermore is easy to reach by the user.

Accordingly, the method in accordance with the invention to control movements of a medical apparatus via a control device with a touch-sensitive display, has at least the steps of selecting an apparatus component of the medical apparatus and moving the selected apparatus component with the requirement that a safety loop is closed in order to activate the movement of the apparatus component. Such a method is suitable for simple control of movements of components of medical apparatuses and serves to prevent damage and injury to users and surroundings due to unmonitored movements of large and heavy apparatus components.

In the method according to the invention, the control is implemented by a control device with a touch-sensitive display. The touch-sensitive display is also known as a touch display. The control device, i.e., the touch-sensitive display, can be operated with one hand or both hands. The user hereby grasps the control device with the display either with one hand or with both hands, with the hand or hands touching the control device both on the front side with the display and on the opposite back side. One-handed operation has the advantage that the user has his or her second hand free, for example in order to additionally hold a body part of the patient and align the apparatus. Two-handed operation has the advantage that (for example) parallel movements of the apparatus components with both hands can be more simply controlled.

According to the invention, the touch-sensitive display of the control device is operated or controlled by touches and gestures on the display, wherein what is known as a contact point is respectively defined or triggered by the contact. In one embodiment, the respective contact point is triggered by at least one finger and/or at least one input element. The input element is a pen-like device that triggers a contact point (also called a touch event) on the display upon contacting the display, analogous to a finger. In the case of a capacitive display, a conductive operating element is used. In the following, contact points are generally discussed independent of whether these are triggered by a finger or an input element. Multiple contact points can also be triggered simultaneously, i.e. when two fingers or two input elements simultaneously touch the display, for example. A parallel displacement of the apparatus component is preferably controlled with two simultaneously triggered contact points.

The respective component of the medical apparatus that is to be moved is selected as a first step. The medical apparatus is, for example, a C-arm system with the C-arm as an apparatus component to be moved, or an x-ray system with the x-ray detector as an apparatus component to be moved. In an embodiment, a specific, predefined region of the display is contacted for selection. A contact point is thus triggered in this region. The predefined region is thereby associated with the defined apparatus component to be selected. For example, multiple regions that are respectively associated with an apparatus component to be selected are located on the display. This is primarily suitable for medical apparatuses in which more than one component is movable and controllable. For identification of the respective regions of the display that are associated with the components, these can be labeled with color or, for example, can display small symbols of the respective component to be moved. In another embodiment, the region of the display that is associated with the respective apparatus component to be selected is associated with a specific finger of a hand of the user and is arranged accordingly on the display.

In the next step of the method according to the invention, the selected apparatus component is moved. The movement of the component is controlled by movement of one or more contact points on the display. The movement of the apparatus component is reflected by the gestures on the display. A defined region on which the contact point or points are moved is advantageously provided at the display for the movement control. In one embodiment, the velocity of the movement of the apparatus component can be controlled. When a first contact point on the display in the defined region is triggered and this is displayed on the display via movement of the finger or of the input element, this produces a movement of the selected component, with the distance between the original contact point and the moved contact point affecting the velocity of the movement. The greater the distance, the faster the movement. The opposite also applies: the smaller the distance, the slower the movement. In another embodiment, the direction is controllable. For example, this can be varied by the alignment of the movement axis, thus the connecting line between an original movement point and a moved contact point. Preferably both the velocity of the movement and the movement direction can be varied and controlled.

Furthermore, a parallel displacement of the apparatus component can be controlled by means of the method according to the invention. This preferably takes place via two simultaneously triggered contact points which are moved together in the same direction with the same velocity.

In order to be able to track the respective controlled movement of the apparatus component on the display, the movement of the contact point on the display is advantageously indicated. This is suitable for a control of the medical without direct eye contact. For example, different colors can be used in order to make it easier for the user to recognize which apparatus component he is presently moving. This feedback to the user in the operation can also be realized by small explanatory graphics. Furthermore, the velocity can be represented by means of a colored bar or, similarly, a speedometer needle. For example, the respective movement vector can be indicated at the display to track the movement direction.

In a preferred embodiment, a virtual joystick is indicated on the display at the original contact point, which virtual joystick also moves and aligns corresponding to the movement of the contact point, and thus visualizes the movement of the apparatus component. In addition to this, color axis markings which correlate to axis markings at the apparatus system can be applied on the region defined for the virtual joystick. Before a component movement, the user can hereby already associate along which axis the movement takes place. The number of failed attempts (meaning incorrectly executed movements) can be reduced. The regions defined for the virtual joystick can likewise be associated with specific apparatus components via a defined coloring. In addition, the colors can be consistently used with the explanation graphics.

According to the invention, an additional safety loop must be closed in order to activate the movement of the apparatus component. Conversely, this means that the movement of the apparatus component is stopped as soon as the safety loop is opened. In a simple embodiment, the safety loop is closed by tapping once on a specific region on the display. Upon tapping (either with a finger or an input element), a contact point is triggered for a short period of time, which closes the safety loop. A continuous contact of the corresponding region on the display is unnecessary. As soon as the safety loop is closed by an initial contact, the apparatus component can thus be moved.

Another embodiment provides that the safety loop is closed by continuous contact with a specific region on the display or a switch at the control device. The safety loop can consequently be closed by continuous contact with a specific region on the display or continuously holding a switch, for example on the back side of the control device. Here a closing of the safety loop is necessary during the entire control process. The movement is stopped and terminated as soon as the safety loop is opened, thus when the contact with the region or the switch ends.

The region on the display that is to be contacted is, for example, a separate region of the display. The region can be the same region in which the movement is controlled. In a simple embodiment, the safety loop is opened by triggering the contact point for movement control and is closed with the end of the movement control.

The invention further concerns a control device to control a medical apparatus, having at least one touch-sensitive display and a dead man's device with a safety loop. In one embodiment, the control device is a mobile control device, for example similar to a wireless remote control. In another embodiment, the control device is a stationary control device, for example in the form of a stationary control panel or a control device arranged directly at the medical apparatus to be controlled. The control device is suited both for mobile operation and for stationary operation. For this, a mobile, wireless control device can be used together with a docking station. If the control device is located in a docking station, it is operated as a stationary control device and can simultaneously be charged. As soon as the control device is removed from the docking station, it can be used as a mobile control device.

According to the invention, the control device has a dead man's device with an additional safety loop. The dead man's device is used in order to prevent unintended triggering of movement of the apparatus components. In one embodiment, the dead man's device is a defined region on the display upon contact with which (with a finger or an input element) the safety loop is closed. In another embodiment the dead man's device is a switch. The switch is preferably arranged at a region of the control device that is easy to access, such that both two-handed operation of the control device and one-handed operation of the control device are possible. The switch is arranged on the back side or a side region of the control device. A simple contact with the switch and closing of the safety loop is possible as soon as the control device is taken in hand by the user. The safety loop is accordingly opened if the switch is released, for example if the user drops the control device. The switch is, for example, a capacitive sensor, a pressure switch or a toggle switch etc.

The control device is suitable for implementation of the method according to the invention as described above.

The invention also encompasses a medical apparatus having at least one apparatus component, wherein the medical apparatus can be controlled by a control device according to the invention as described above by execution of a method according to the invention as described above.

The invention described above provides the advantages are that the control by a control device with touch-sensitive display can be integrated into existing operating concepts with a touch-sensitive display. This entails both a cost advantage and advantages in application.

A specific example of such an integration is the combination of a touch display-based control of a diaphragm (advantageously of a radiography or fluoroscopy apparatus) with its movement control. Here a single control device with a touch display offers both functions to control apparatus component movements and to control the diaphragm, either simultaneously or after being switched over.

Another advantage is that changes at the apparatus itself can simply be transferred to its control at the display and vice versa, since no (or only slight) changes to the control device are necessary.

Another advantage is that a completely or partially blind operation (thus without visual contact with the apparatus to be moved or the control device) is possible. The proportion of movements which can be controlled with visual contact with the medical apparatus depends on the reproduction and presentation of the system movements at the display. The more precisely that the controlled movements are presented at the display, the less visual contact is necessary in order to monitor the controlled movements. For example, if the presentation of the movements is implemented so that it appears in a defined region of the display, the proportion in which the operation can be executed without visual contact is very high. Accordingly, it is also advantageous that the control of movements of the apparatus components can be combined with direct visual feedback on the display.

Overall, the method according to the invention offers the advantage that complex movement of a component of a medical apparatus are controlled via small gestures and movements on the touch-sensitive display of the control device. The method according to the invention thereby supports a simple integration of an additional safety loop, for example via a capacitive sensor mounted on the back side of the control device or via a defined region on the display. The safety loop can be closed by a simple hand grip or simply by triggering contact points in order to execute the movements of the medical apparatus.

DESCRIPTION OF THE PREFERRED EMBODIMENTS

Figure 1:
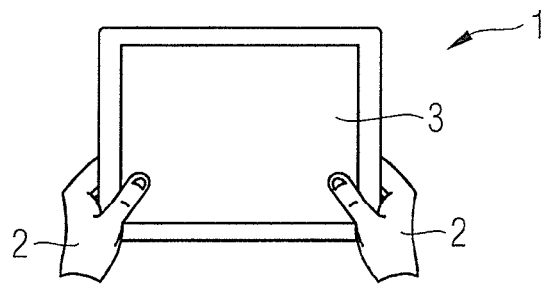
FIG. 1 is a schematic presentation of a front side of a mobile control device in accordance with the invention, to be operated with two hands.
Figure 2:
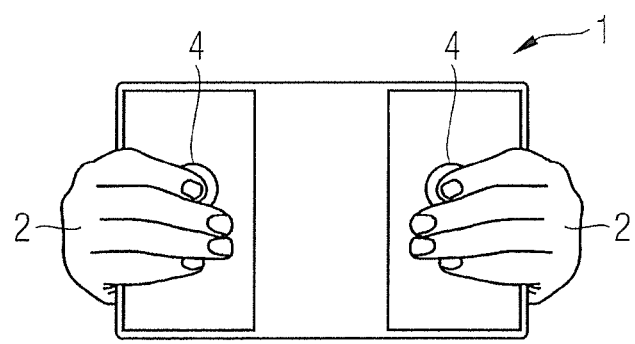
FIG. 2 is a schematic presentation of a back side of the control device according to FIG. 1.

FIGS. 1 and 2 show a control device 1 with a touch-sensitive display 3. The control device 1 is designed for two-handed mobile use. Accordingly, both hands 2 of a user are shown, which grip the control device 1 on two opposite sides. The thumbs rest on the display 3 on a front side of the control device 1 (see FIG. 1) and the other four fingers rest on a back side (see FIG. 2). Movement of a component of a medical apparatus can be controlled with movements of a digit (here the thumbs) on the display 3 (see FIGS. 4, 5 and 7).

Two capacitive sensors 4 are mounted on the back side of the control device 1 (see FIG. 2). One finger of a hand 2 rests on each of the sensors 4. A safety loop is closed by touching the sensors 4, such that a movement of a preselected component of a medical apparatus is possible.

Figure 3:
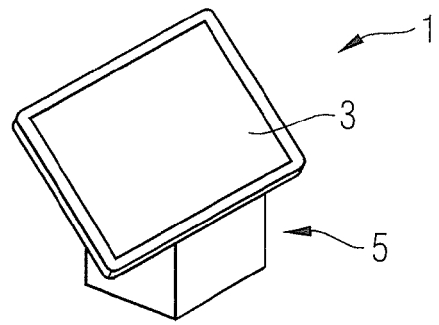
FIG. 3 is a schematic presentation of the mobile control device according to FIG. 1 in a docking station.

A schematic depiction of the mobile control device 1 according to FIG. 1 is shown in a docking station 5 in FIG. 3. The control device 1 is connected (for example firmly clamped) on its back side with the docking station 5 so as to be detachable. The control device 1 is thus arranged in the docking station so that a hand position as it is shown in FIGS. 1 and 2 continues to be possible. The user thus continues to easily reach the sensors 4 on the back side of the control device 1. In the docking station 5, the control device 1 is used as a stationary control device 1. A simple operation with only one hand is thus also possible. Furthermore, the control device 1 can be charged via the docking station 5.

Figure 4:
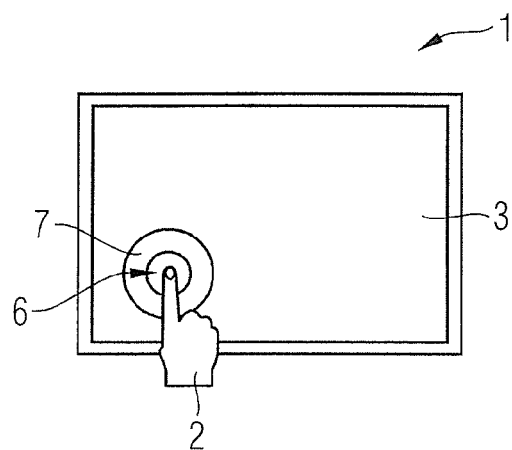
FIG. 4 is a schematic presentation of the control device in accordance with the invention, with a first control situation.
Figure 5:
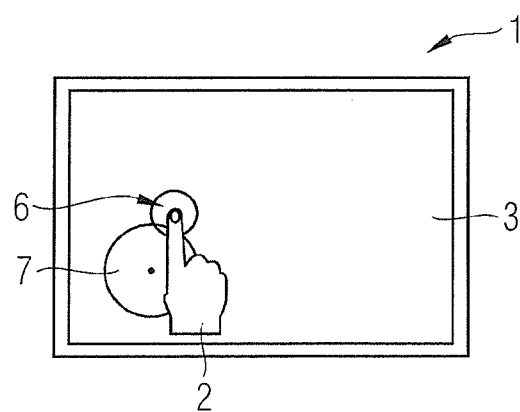
FIG. 5 is a schematic presentation of the control device according to FIG. 4 with an additional control situation.

FIGS. 4 and 5 show a schematic presentation of a control device 1 with various control situations. The control device 1 shown here is operated with one hand, more precisely stated with an index finger of the right hand 2 of a user. The tip of the index finger touches the display 3 and thus triggers a contact point 6 (see FIG. 4). For a simplified operation and for graphical depiction, a virtual joystick 7 is shown at the contact point 6 in the form of two concentric circles arranged around the contact point 6. The virtual joystick facilitates the operation in that it gives the user a direct feedback about the movement control. If a translation movement should be executed in a specific direction, the index finger is shifted in this direction on the display. This control situation is shown in FIG. 5. The virtual joystick 5 thereby together moves with the finger movement in that—according to this embodiment—the inner circle follows the contact point 6 and moves together with the tip of the index finger. The further that the contact point 6 moves from its initial position, the more quickly that the transition movement is executed.

Figure 6:
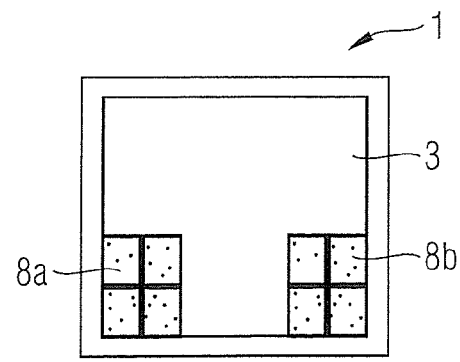
FIG. 6 is a schematic presentation of a control device in accordance with the invention, with labeled control regions.

FIG. 6 shows a schematic presentation of a control device 1 with labeled control regions 8a and 8b. The control regions 8a and 8b are respectively arranged in one corner of the display 3 so that these are easy to reach by the hand of the user. Both control regions 8a and 8b can be associated with a respective specific apparatus component or a specific movement of the apparatus component. This facilitates an intuitive control for the user. Furthermore, the vertical and horizontal movement axes are respectively shown in the control regions 8a and 8b. This likewise makes the movement control easier for the user.

Figure 7:
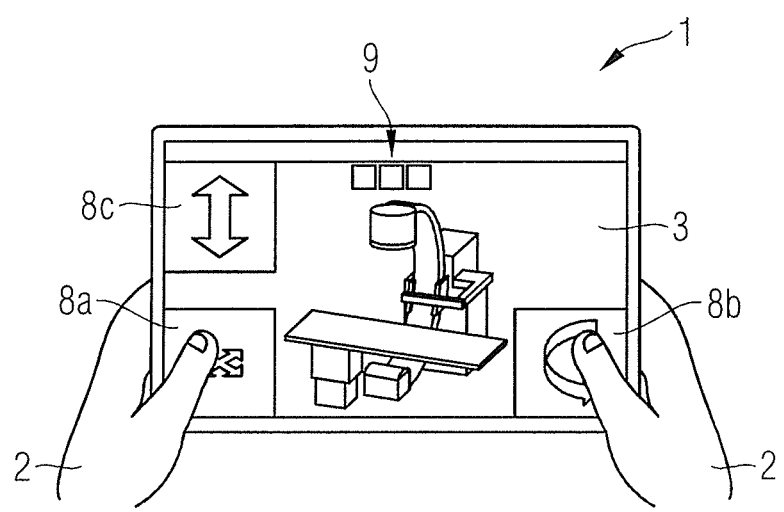
FIG. 7 is a schematic presentation of a control device in accordance with the invention, with various control regions associated with a respective apparatus component.

FIG. 7 shows a schematic presentation of a control device 1 with various control regions 8a through 8c associated with a respective apparatus component. In this embodiment, the control device 1 is designed for mobile, two-handed operation. The hands 2 of the user hold the control device 1 on two sides (see FIG. 2). The thumbs are arranged on the display 3, and the other fingers on the back side of the control device 1 (see FIG. 3).

The three control regions 8a, 8b and 8c are arranged in three corners of the display 3. Each of the three control regions 8a, 8b and 8c is associated with a defined movement, which is indicated by the different arrows in the control regions 8a, 8b and 8c, namely horizontal translation movement, rotation movement, and vertical translation movement. In an upper region of the display 3, three selection fields 9 are executed in a predefined region. These selection fields 9 are associated with a respective apparatus component to be controlled. The medical apparatus to be controlled here are an x-ray system which is shown in the background at the display 3. For example, one selection field is associated with the patient table and one selection field is associated with the x-ray radiator.

According to the method according to the invention, an apparatus component to be moved is selected in a first step. This takes place by tapping on the respective selection field. As a next step, the selected apparatus component is moved in that the respective desired movements are executed via gestures on the display 3 in the respective control regions 8a, 8b or 8c. For safety engineering reasons, the system movements are possible only possible if an additional safety loop at the control device 1 is closed. In the embodiment shown here, the safety loop via a capacitive sensor on the back side of the control device 1 is closed by a continuous contact with the fingers (see FIG. 3).

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to control a movement of a component of a medical apparatus via a control device having a touch-sensitive display, comprising:
   via a touch-sensitive display screen of said touch-sensitive display, receiving an input that selects an apparatus component of the medical apparatus that is to be moved, by contact of a thumb of an operator with said touch-sensitive display screen;
   emitting a control signal from the control device to the selected component that causes movement of the selected component at said medical apparatus;
   providing a sensor at a side of said touch-sensitive display opposite said touch-sensitive display screen;
   forming a safety loop in said control device that includes said touch-sensitive display screen and said sensor; and
   requiring said safety loop to be closed by simultaneous and continuous contact of the thumb of the operator with said touch-sensitive display screen and a finger of the operator on said sensor, in order to activate said movement of said apparatus component.

2. A method as claimed in claim 1 comprising configuring the touch-sensitive display to be operable with one hand.

3. A method as claimed in claim 1 comprising configuring the touch-sensitive display to be operable with two hands.

4. A method as claimed in claim 1 comprising selecting said apparatus component by contacting a defined region of the touch-sensitive display that is individually associated with said apparatus component.

5. A method as claimed in claim 1 comprising automatically and immediately stopping movement of said selected apparatus component if said safety loop does not remain closed.

6. A control device to control movement of a component of a medical apparatus, said control device comprising:
   a touch-sensitive display comprising a touch-sensitive display screen at a first side of said touch-sensitive display, and a sensor at a second side of said touch-sensitive display, opposite said first side;
   said touch-sensitive display screen of said touch-sensitive display receiving an input that selects an apparatus component of the medical apparatus that is to be moved, by contact of a thumb of an operator with said touch-sensitive display screen;
   said touch display being configured to emit a control signal to the selected component that causes movement of the selected component at said medical apparatus;
   a safety loop in said control device that includes said touch-sensitive display screen and said sensor; and
   said touch display being configured to require said safety loop to be closed by simultaneous and continuous contact of the thumb of the operator with said touch-sensitive display screen and a finger of the operator on said sensor, in order to activate said movement of said apparatus component.

7. A medical apparatus comprising:
   a plurality of movable medical apparatus components;
   a control device comprising a touch-sensitive display comprising a touch-sensitive display screen at a first side of said touch-sensitive display, and a sensor at a second side of said touch-sensitive display, opposite said first side;
   said touch-sensitive display screen of said touch-sensitive display receiving an input that selects an apparatus component of the medical apparatus that is to be moved, by contact of a thumb of an operator with said touch-sensitive display screen;
   said control device being configured to emit a control signal to the selected component that causes movement of the selected component at said medical apparatus;
   a safety loop in said control device that includes said touch-sensitive display screen and said sensor; and
   said control device being configured to require said safety loop to be closed by simultaneous and continuous contact of the thumb of the operator with said touch-sensitive display screen and a finger of the operator on said sensor, in order to activate said movement of said apparatus component.

* * * * *